(12) United States Patent
Nimberger et al.

(10) Patent No.: US 6,289,752 B1
(45) Date of Patent: Sep. 18, 2001

(54) SAMPLING SYSTEM

(75) Inventors: Spencer M. Nimberger; Kevin J. Cessac, both of Houston, TX (US)

(73) Assignee: Pgi International, Ltd., Houston, TX (US)

( * ) Notice: Subject to any disclaimer, the term of this patent is extended or adjusted under 35 U.S.C. 154(b) by 0 days.

(21) Appl. No.: 09/618,512

(22) Filed: Jul. 18, 2000

(51) Int. Cl.$^7$ .................................................... G01N 1/00
(52) U.S. Cl. ..................................... 73/863.11; 73/863.86
(58) Field of Search ............. 73/863.11, 863.81–863.86, 73/864, 864.33–864.35

(56) References Cited

U.S. PATENT DOCUMENTS 4,974,455 * 12/1990 McGowan et al. ............... 73/863.12
5,498,138    3/1996 Nimberger et al. .
5,531,130 *  7/1996 Welker ............................. 73/863.11

* cited by examiner

*Primary Examiner*—Robert Raevis
(74) *Attorney, Agent, or Firm*—Browning Bushman (57) ABSTRACT

A system for a sampling hydrocarbon containing gas flowing in a pipeline by collecting a fluid sample in a sampler bottle 55 includes a sample probe 12 secured to and extending outward from the pipeline, a heater body 20 removably secured to the probe, and vortex heater 34 for outputting a cold fluid and hot fluid. The heater body 20 has flow path therein for directing the hot fluid to heat the sample probe, and preferably thereafter heat the bottle 55. The pressurized gas to the vortex heater may be supplied directly from the pipeline P, with pressure control by a regulator 24. Alternatively, pressurized gas such as air may be stored in a portable vessel 172 for supplying compressed air to the vortex heater 34. An improved method of sampling gas in a pipeline using the vortex heater is disclosed.

27 Claims, 6 Drawing Sheets

SAMPLING SYSTEM

FIELD OF THE INVENTION

The present invention relates to sampling systems and techniques suitable for sampling a media in a flowing pipeline. More particularly, the present invention relates to a spot sampling technique for periodically filling a cylinder or a portion of a sample cylinder with a hydrocarbon-containing gas in the flowing pipeline at selected time intervals for subsequently analyzing the constituents of the sample and assuming that the sample constituents represent the flowing media.

BACKGROUND OF THE INVENTION

Those familiar with the technology of sampling a hydrocarbon-containing media, such as natural gas, in a flowing pipeline recognize that there are two well-known sampling techniques:

(1) "Spot sampling" involves the taking of a sample of media at one or more points in time and assuming that the sample accurately represents the composition of the media over some defined substantially long period of time, e.g. one sample per week or once per month. The spot sampling method may thus involve simply filling a sample cylinder containing a vacuum with the media, with the decision to spot sample requiring interaction by a sampler technician. More typically, a sample cylinder may be conditioned by a series of fill and empty actions to remove all air and then finally fill the cylinder to take the samples.

(2) "Composite sampling" differs from spot sampling in that in composite sampling method, the media in a flowing pipeline collects the sample media slowly over some defined long period of time. Prior to starting the composite cycle, the sample cylinder may thus be conditioned using a repeating, fill and empty method, and the sample cylinder then left at ambient pressure. The composite cycle is typically performed by a positive displacement sample pump that samples a fixed volume or "bite" of media at a rate proportional to the flow, e.g., taking a selectively sized sample "bite" once every several thousand cubic feet of flowing gas. Less accurately, a sample of a fixed size may be taken once every several minutes, and typically from once every two minutes to once every sixty minutes. In yet another composite sampling technique, a small sample slowly "leaks" to the sampler bottle using a motorized regulator. The point is that the sampling equipment, not a sampling technician, determines when a sample bite is obtained.

Both the spot sampling and composite sampling techniques have historically been performed without regard to the ambient temperature of the sampling equipment or the dew point of the gas being sampled. During the act of obtaining a sample, the gas may be brought below its dew point by coming into contact with sampling equipment that is at a temperature below the dew point of the flowing gas. In this situation, components of the sampled gas will tend to condense out and cling to the walls of the sampling equipment. Since the condensed components of the gas are commonly the heavy ends that are rich in BTU content, and since these condensed components never get into the sample cylinder because they cling to the walls of the equipment or drip back into the pipeline, the sample which is taken is biased "lean", meaning that the BTU content of the gas flow into the pipeline is actually greater than that represented by the sample.

The above deficiencies in sampling equipment have long been recognized by the American Petroleum Institute (API). API has recently enacted a sampling standard that requires heating of the sampling equipment to a temperature above the dew point of the flowing gas while the sample is being taken. Cost effective and efficient solutions to the heating requirement are formidable, since typically electrical power is not available at the sampling point. Gas is plentiful and infra-red heater solutions are possible with composite samplers because they must be kept warm over an extended period of time. The sampling speed required with spot sampling, however, makes the infra-red heater solutions inefficient because of their long start-up cycle times. A prior art sampling pump with a pressure regulator is disclosed in U.S. Pat. No. 5,498,136.

The disadvantages of the prior art are overcome by the present invention, and an improved sampling system and method particularly applicable for spot sampling is disclosed. The present invention thus overcomes many of the difficulties and shortcomings of the prior art, which have long been recognized in the industry.

SUMMARY OF THE INVENTION

The sampling system and technique of the present invention is primarily directed to spot sampling, not composite sampling. The technique of the present invention is cost effective since only the probe must be purchased for each spot sampling site. A heater/sampler attachment is thus necessary only for each sample technician, who reuses this equipment at each sample point. Cross-contamination may be substantially reduced if not entirely eliminated by a simple cleaning operation between samples. Only a short section of a straight small diameter hole connecting the probe to the sample cylinder need be cleaned for most applications.

The power for heating may be obtained from the gas being sampled and the heat is generated in an intrinsically safe manner using a vortex heater. Most components of the system are fabricated from a hard annodized aluminum which provides both excellent corrosion resistance and quick heat up times, since aluminum is an excellent heat conductor. Alternatively, pressurized gas to the vortex heater may be supplied by a portable pressurized gas vessel, such as a compressed air bottle.

It is an object of the present invention to provide an improved technique for sampling that satisfies the desire that the sampling equipment be heated to a temperature above the dew point of the flowing gas while the sample is being taken.

A related object of the invention is a sampling system which utilizes a vortex device responsive to the fluid in the pipeline to heat the sample probe and sampler bottle. The heating/sampling device may be manually oriented and connected to a permanently installed hot gas circulating probe.

It is a further object of the invention to provide an improved method of sampling wherein the probe and sampler bottle are heated with the medium being circulated in the pipeline. A sampler bottle is exposed to externally circulating hot gas constrained to an annulus about the OD of the sampler bottle.

Yet another object of the invention is an improved method of heating a sample probe and bottle prior to taking a spot sample, with a method utilizing hot fluid from the flowing media to heat the sampling equipment while the sample is being taken.

It is a feature of the invention that the sampler bottle may thus be mounted directly to the sampler body.

The sampling equipment may include a removable bottle sheath with a slot running the length of the sheath and containing a split pliable material to provide hot gas sealing while allowing the sheath to be placed over the sampler bottle in the presence of valves on either end of the bottle.

A feature of the present invention is that the sampling equipment and method may be reliably used by sampling personnel with little training and experience.

Yet another feature of the invention is the substantially improved sampling accuracy and the resulting savings realized when conducting spot sampling of a medium, such as natural gas, flowing in a pipeline.

Still another feature of the invention is that the components of the sampling equipment may be easily manufactured to have a relatively long life. The system is highly reliable and cost effective. Only the probe must be purchased for each spot sampling site.

Yet another feature of the invention is that cross contamination of the sampled fluid may be substantially reduced if not entirely eliminated.

Yet another feature of the invention is that the power source for obtaining heat is generated in an intrinsically safe manner.

Yet a further feature of the invention is that most of the components of the sampling system may be fabricated from aluminum.

These and further objects, features, and advantages of the present invention will become apparent from the following detailed description, and reference is made to figures in the accompanying drawings.

DETAILED DESCRIPTION OF PREFERRED EMBODIMENTS

Figure 1:
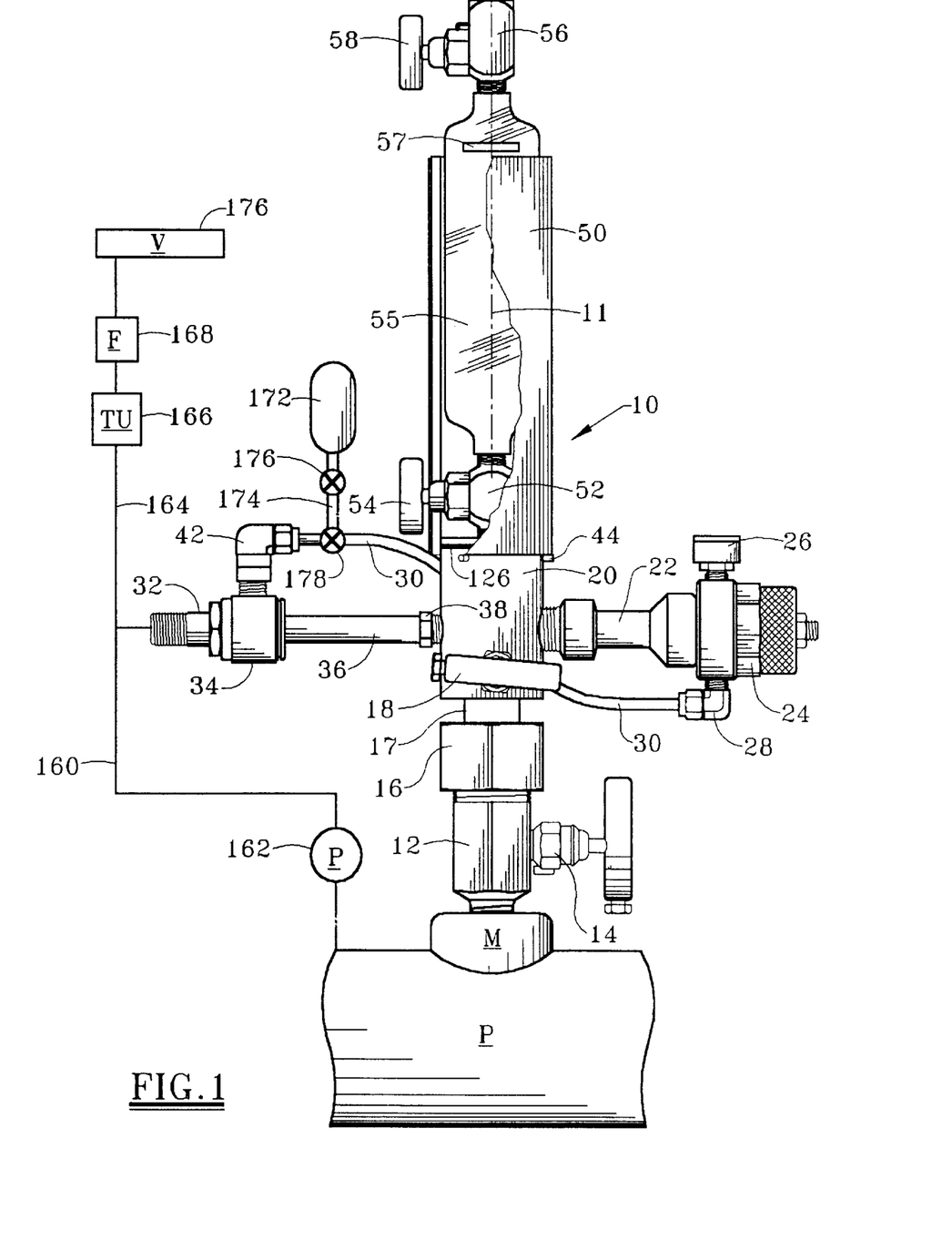
FIG. 1 is a simplified pictorial view of one embodiment of a spot sampling system according to the present invention installed on a pipeline.

FIG. 1 illustrates one embodiment of a suitable system for sampling gas flowing in a pipeline. More particularly, the system 10 for sampling the gas in the pipeline P may be used to collect a fluid sample in a sampler bottle, such as sampler bottle 55 discussed subsequently. In a representative application, the sampling system may be at a remote location where electrical supply lines are not readily available. The fluid flowing through the pipeline P may be natural gas or another hydrocarbon containing gas, such as hexane, butane, pentane, propane, or mixtures thereof with other hydrocarbon containing gasses.

The system 10 includes a sample probe 12 which is secured to and extends rapidly outwardly from the pipeline P. In an exemplary application, the pipeline P includes a mounting M for sealing engagement with the sample probe 12. As discussed subsequently, the sample probe 12 has an inlet for positioning within the gas flowing through the pipeline, such that natural gas in the pipeline P may pass through the sample probe 12, through the heater body 20, and be collected in the sampler bottle 55. The heater body 20 is removably secured to the probe, preferably by threaded engagement, and transmits gas from the sample probe to the sampler bottle. A vortex heater 34 is provided for receiving compressed gas, and separately outputting a cold fluid and a hot fluid, as explained subsequently. In an exemplary application, natural gas is passed through the sample probe 12 and a portion of the heater body 20, and is then transmitted via threaded conduit 22 to regulator 24 so that the fluid pressure in line 30 which connects the regulator 24 with heater body 12 is at a select pressure which is lower than the pressure in the pipeline. Valve 178 in the line 30 is optional, as explained subsequently, and for purposes of this example may be eliminated.

Figures 2, 3:
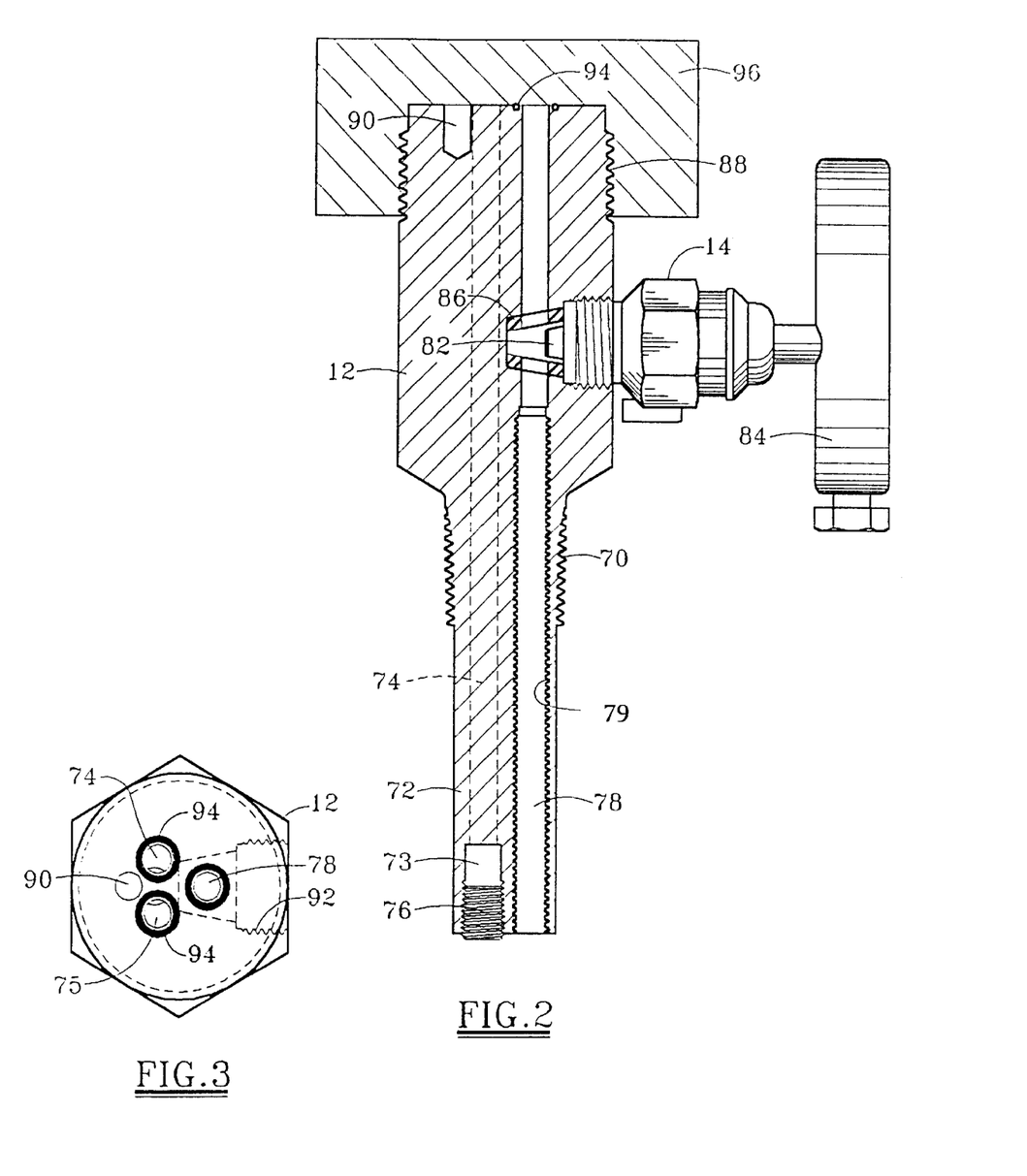
FIG. 2 is a cross-sectional view of the sample probe generally shown in FIG. 1.
FIG. 3 is top end view of the probe shown in FIG. 2.

Those skilled in the art appreciate that the sample probe 12 may include a conventional sample probe valve 14 for retaining pressurized fluid in the pipeline P. Referring briefly to FIGS. 2 and 3, sample probe 12 may thus be directly threaded to the mounting M on the pipeline via external threads 70, so that the sample probe 12 is both fixed to the pipeline P and is sealingly connected to the mounting M. The fluid in the pipeline thus flows upward through the passageway 78 shown in FIG. 2, and is normally retained in the pipeline by the closed valve 14. Threads 88 at the upper end of the body 12 may be provided for providing for receiving a covering or cap 96, which protects debris from falling into the passageways in the sample probe 12 and protects the threads 88 from damage. The valve 14 includes a conventional handle 84 for moving the valve member 82 into and out of sealing engagement with the seat 86, which in a preferred embodiment may be elastomeric or "soft" seat. The soft material cone seat 86 is ideal since it provides a straight through passage of fluid through the passageway 78 when the valve is in the open position. In other embodiments, the valve member may move into engagement with a metallic or "hard seat." In a preferred embodiment, the inner wall of at least that portion of the fluid passageway 78 which is positioned within the pipeline P is preferably provided with an irregular sidewall to aid in retention of condensation. Rather than being a straight cylindrical-shaped passageway, the sidewall 79 may thus be threaded to provide an acceptable irregular sidewall in at least a lower portion of the passageway 78 which is positioned within the pipeline. The body 12 also includes a locating hole 90, which will be discussed subsequently.

As shown in FIGS. 2 and 3, both a hot fluid incoming passageway 74 and hot fluid outgoing passageway 75 are also provided in the probe 12. As explained subsequently, hot fluid thus moves downward from the upper end of the body 12 to the lower end 72 of the body 12, thereby warming the probe and thus the gas in the passageway 78. At the lower end of the probe, a connecting passageway 73 is provided for fluidly interconnecting the hot fluid incoming passageway 74 with the hot fluid outgoing passageway 75. In effect, the hot fluid thus flows downward along the elongate incoming passageway 74, is turned in a generally U-shaped direction by the passageway 75, then goes up the parallel outgoing hot fluid passageway 75. A plug 76 may be provided at the lower end of each of the passageways 74 and 75 for plugging the lower end of each passageway. A conventional O-ring or other sealing member 94 may be provided on the upper end of the body 12 for sealing each of the passageways 74, 75, and 78 with a suitable heater body, as described subsequently. FIG. 3 depicts a threaded port 92 in the side of the body 12 for receiving the probe shut-off valve 14, as discussed above.

Figure 4:
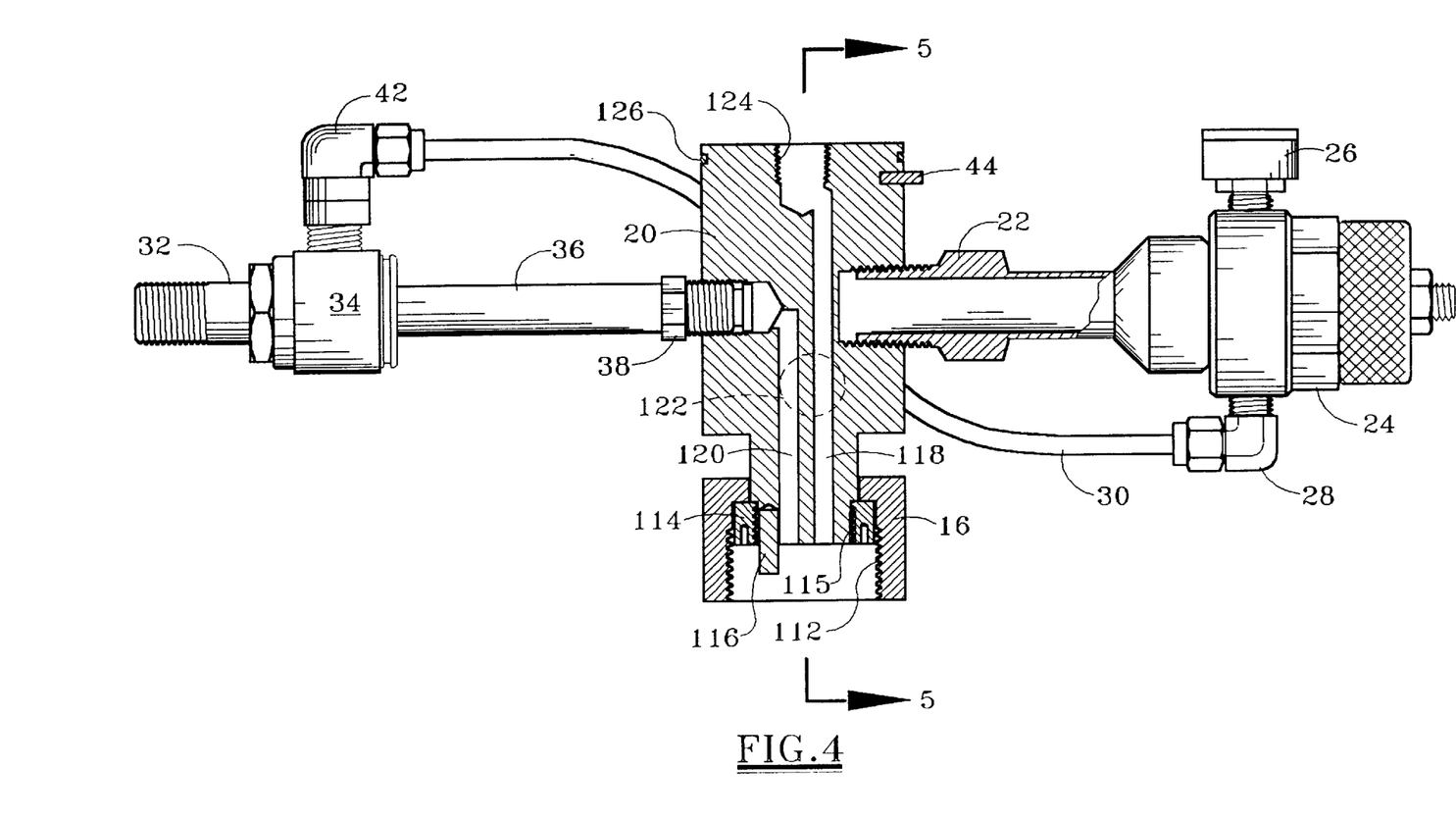
FIG. 4 is a side view, primarily in cross-section, of a heater body, a vortex heater and regulator as generally shown in FIG. 1.

Referring now to FIGS. 1 and 4, the natural gas in the pipeline P thus flows through the passageway 78 in the probe 12 and, assuming the valve 14 is open, then flows into the passageway 118 in the heater body 20. The lower end 17 of the body 20 may be sized for receiving union nut 16 which structurally connects the heater body 20 with the sample probe 12. Natural gas from the pipeline P thus flows through a portion of the heater body 20 and into the regulator 24. Conventional pressure gauge 26 may be used for monitoring the outlet pressure from the regulator. Connector 28 fluidly connects one end of the tubing 30 to the regulator 24, while similar connector 42 connects the opposing end of the tubing 30 to the vortex heater 34. A suitable vortex heater according to the present invention may be the Model 3230 vortex heater manufactured by Exair Corporation.

The vortex heater 34 thus receives pressurized gas, and the vortex action within the heater provides for the separate output of a cold fluid through the cold fluid line 32 and a hot fluid through the hot fluid line 36. A connector 38 thus connects the hot fluid line 36 to the heater block 20, as shown in FIG. 4. Hot fluid thus moves down the elongate cylindrical passageway 120 to the heater block 20, with the passageway 120 being in fluid communication with the incoming hot fluid passageway 74 in the probe 12. Hot fluid then flows back upward through the outflowing hot fluid passageway 75 in the probe and into the elongate fluid passageway 118 in the heater body 20.

FIG. 4 depicts the union nut 16 with internal threads 112 for threaded engagement with the external threads 88 on the probe 12. When it is desired to take a sample, the sampler technician may thus remove the cap 96 from the upper end of the probe 12 as shown in FIG. 2, then thread the union nut 16 onto the probe to fixedly interconnect the heater body with the probe. The connector 22 as shown in FIG. 4 may be formed from 316 stainless steel with a desired thin wall to provide thermal isolation. Threads 115 may be provided for rotationally securing the union shoulder nut 114 to the body 20. Pin 116 may be fixed to the heater body 20 for receipt within the hole 90, as shown in FIG. 2, thereby rotationally aligning and locking in place the position of the heater body with respect to the probe. Union shoulder nut 114 may thus be threaded to the body 20 and serves as a stop for withstanding the axial force caused during the torqued engagement of the union nut 16 with the upper planer surface of the probe 12. The O-ring seals 94 as shown in FIG. 3 thus provide the desired fluid-tight communication between the passageways. FIG. 4 illustrates the position of the threads 112 for receiving the valve 18 which controls fluid flow to regulator 24.

Figure 5:
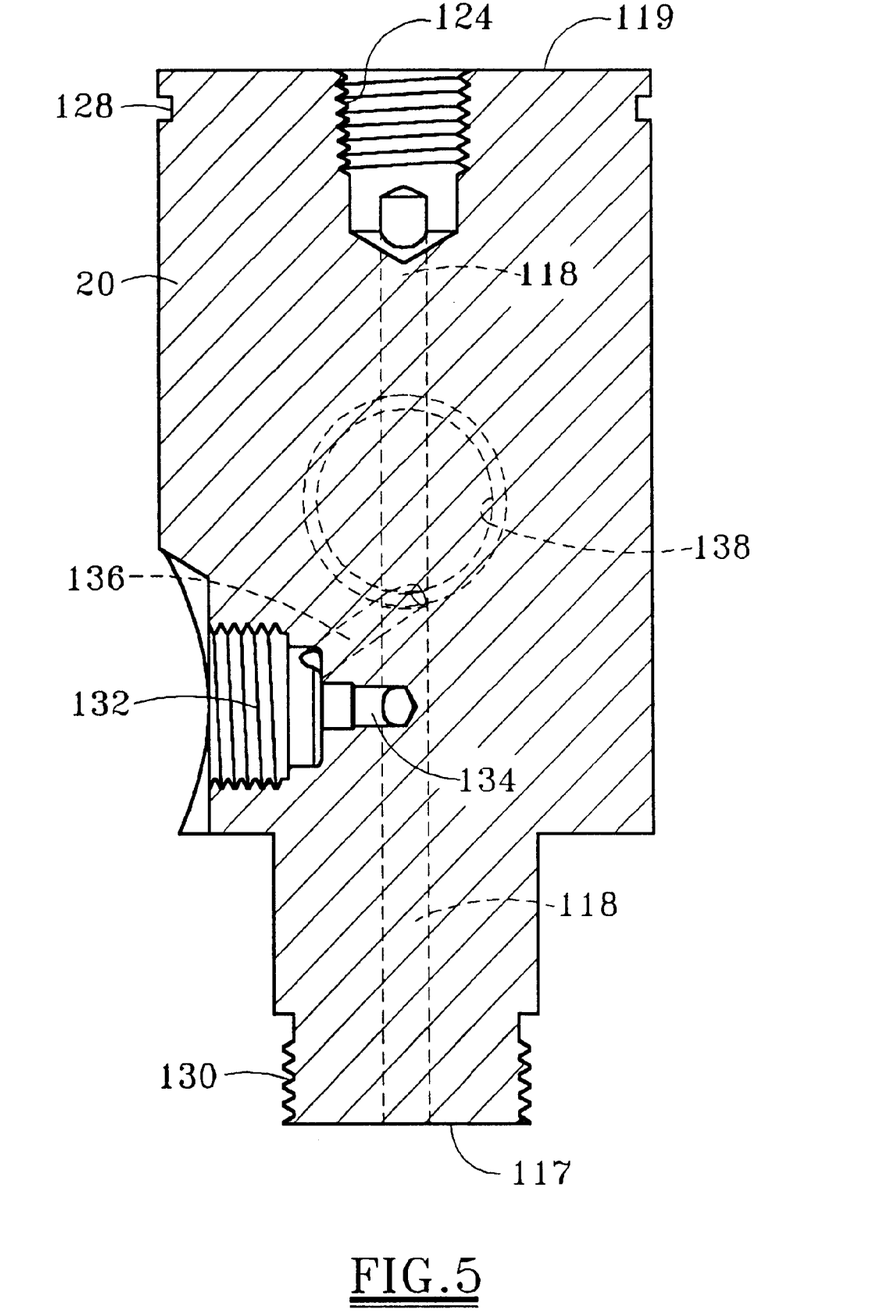
FIG. 5 is a cross-sectional view of the heater body taken along lines 5—5 in FIG. 4.

FIG. 5 is a cross sectional view along lines 5—5 in FIG. 4. In this view, the heater body 20 is shown to include a threaded port 132 for receiving the valve 18. The position of the threaded port 138 for receiving the conduit 22 is also shown. The linear fluid passageway 118 is provided between a lower planar surface 117 and an upper planar surface 119 on the body 20. The upper end of the passageway 118 may include a threaded port 124 for threading engagement with a lower isolation valve 52 as shown in FIG. 1. FIG. 5 depicts the flow passageway 134 for fluidly connecting passageway 118 with port 132, and also the flow passageway 136 which fluidly connects the threaded port 132 with the threaded port 138. The connecting passageway 136 thus provides high pressure gas to the regulator 24, with upstream pressure to the regulator being controlled by valve 18. The threads 130 on the lower neck section of the body 112 are thus intended for engagement with the union nut 16.

Returning now to FIG. 1, the lower isolation valve 154 may be controlled for opening or closing the flow of pressurized fluid from the gas inlet passageway 118 in the heater body, which is fluidly connected to the inlet passageway 78 in the probe 12, with the interior of bottle 55. Conventional bottle 55 may be formed from any desired material, such as an aluminum bottle currently available from Parker Hannifin. Bottle 55 is also provided with an outlet or discharge valve 56. Those skilled in the art will appreciate that the valve 57 as shown has a central axis aligned with the central axis 11 of the bottle 55, which is also the central axis of the fluid passageway in the lower isolation valve 52 and at least the portion of the probe 12 extending radially outward from the pipeline P. Rotation of handle 54 thus opens or closes the valve 52, and rotation of handle 58 similarly opens and closes the valve 56. In alternate arrangements, the valves 52 and 56 and the bottle 55 may be positioned other than as shown in FIG. 1.

FIG. 1 also depicts a sheath 50, which acts as a warming sheath for the bottle. A suitable sheath 50 may be fabricated from a PVC material, and is discussed further below with respect to FIGS. 8 and 9. For the present, it should be understood that hot fluid from the vortex heater 34 moves through passageways in the probe 12 to warm the sampling fluid passageway in the probe, with the hot fluid line then passing through passageway 120 in heater body 20 and then exiting in the annular gap between the sleeve-shaped sheath 50 and the bottle 55. A plurality of stops 44 may be provided on the heater body 20 for supporting the sheath 50 thereon.

For the embodiment shown in FIG. 1, the upper end of the sheath 50 is terminated at a position shortly below visible temperature indicator 57. Indicator 57 may be a self-adhesive liquid crystal temperature indicator. The indicator 57 thus provides user feedback to determine when the sampling system is warm enough to take the sample. A suitable indicator is the Model RLC/50 Series thermometer available from Omega Engineering. A suitable vortex heater is the Model 3230 heater available from Exair Corporation. A regulator of the type conventionally available from various manufacturers may be utilized in the sampling system of this invention.

Figures 6, 7:
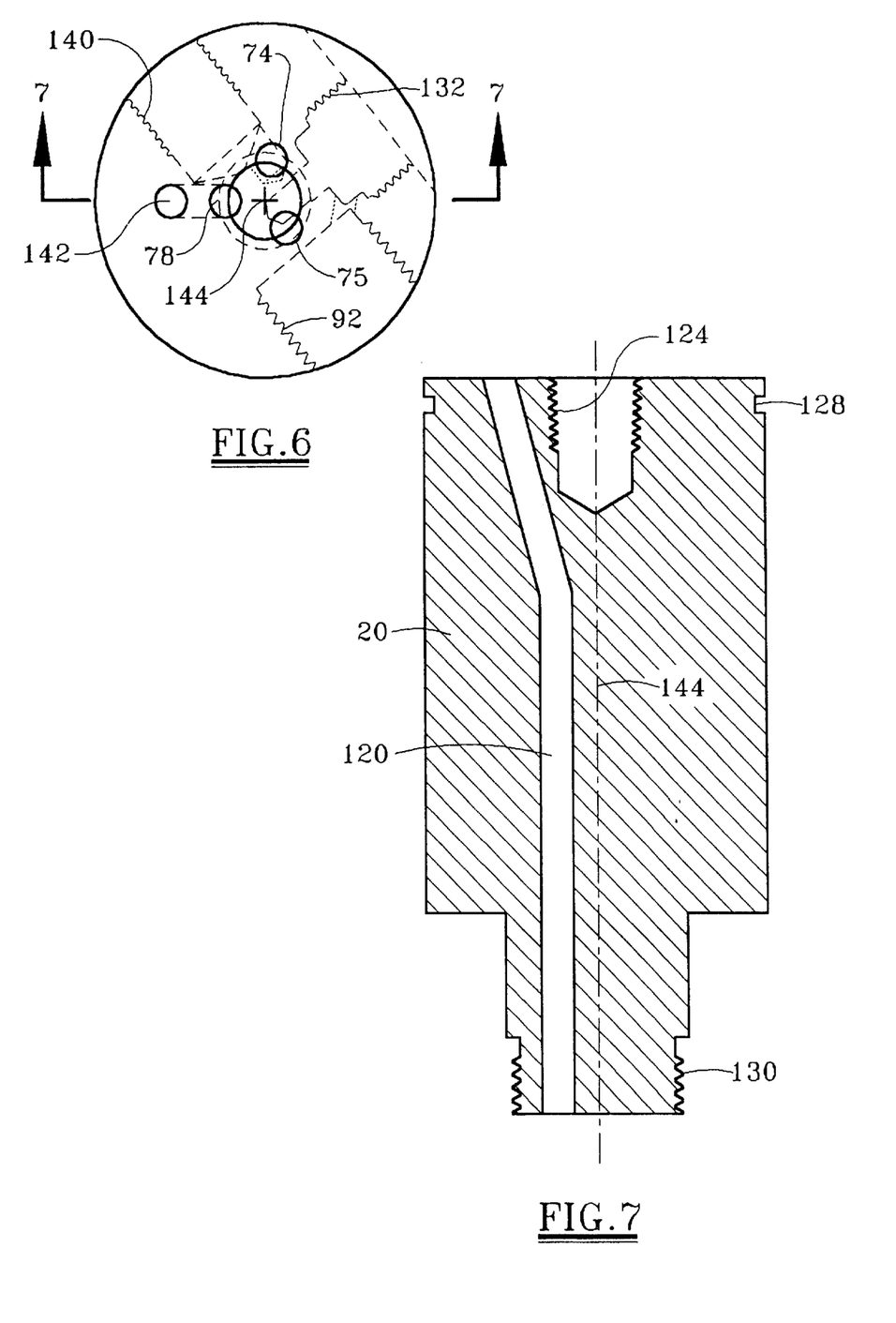
FIG. 6 is top view of the heater body shown in FIG. 5.
FIG. 7 is cross-sectional view taken along lines 7—7 in FIG. 6.

FIG. 6 is a top view of the heater body 20 which is shown in cross section in FIG. 7. The hot fluid passageway 120 in the body thus provides heated gas from the vortex heater 34 to the exterior of the bottle 55, and preferably to the annular gap between the bottle 55 and the warming sheath 50, thereby keeping the bottle warm during the sampling process. A seal 126 as shown in FIG. 4 may fit within a groove 128 as shown in FIG. 6 for substantially sealing a lower end of sheath 50 with the heater body 20.

FIG. 6 depicts the previously discussed fluid passageways 74, 75, and 78, which in a preferred design may be substantially equally spaced about an imaginary circle with its center coincident with centerline 144 of the heater body 20. The position of the threaded port 132, port 92 for conduit 22, and port 140 for connector 38 in the heater body 20 is also shown.

Both the probe 12 and the heater body 20 are preferably formed from a hard anodized aluminum material. This material provides a good combination of corrosion resistance and excellent thermoconductivity.

Figure 8:
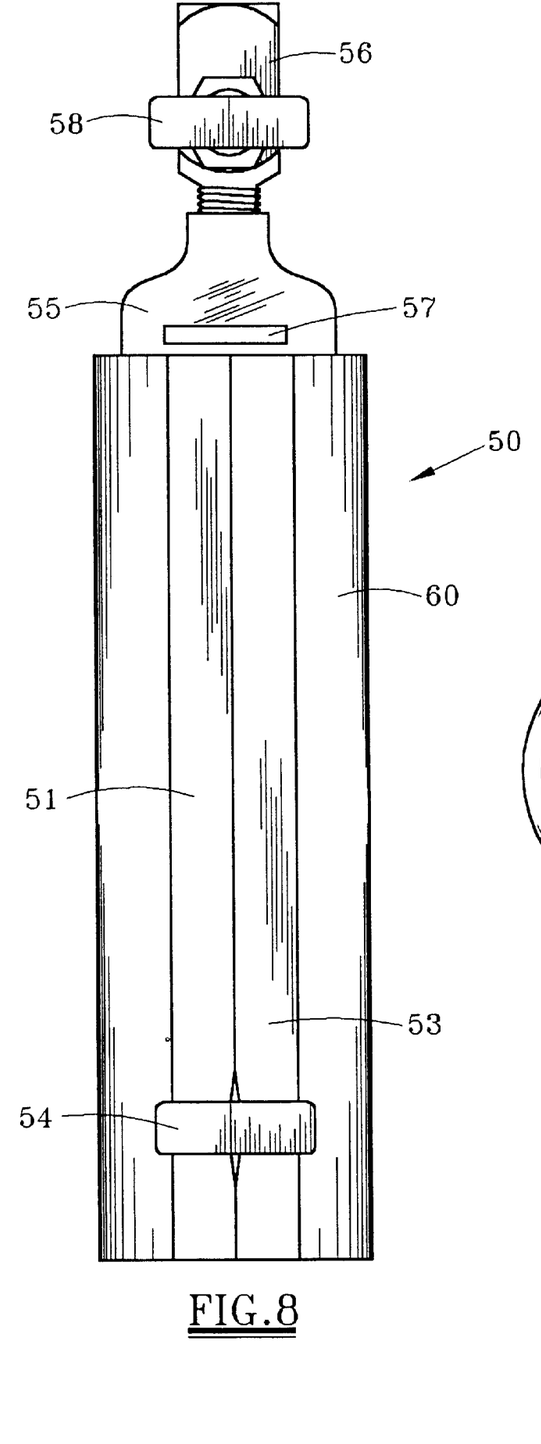
FIG. 8 is a pictorial view of a sampler bottle enclosure generally shown in FIG. 1.
Figure 9:
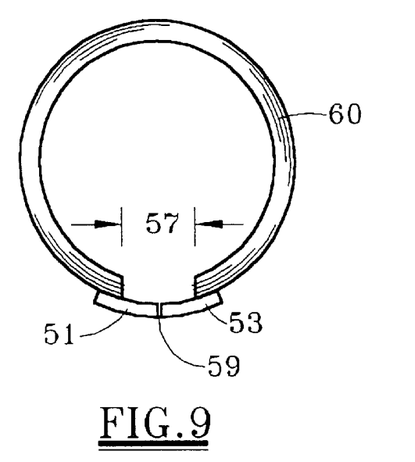
FIG. 9 a top view of the enclosure shown in FIG. 8.

FIG. 8 is a left side view of the sheath 50, depicting an upper portion of the bottle 55 with the temperature display 57, and the upper isolation valve 56 controlled by handle 58. The PVC sheath as shown in FIGS. 8 and 9 may have a substantially C shaped configuration, with a gap 57 between the sides of an elongate cut. In a typical application, the sheath may have an internal diameter of 2.1 inches, and gap 57 may have a circumferential length of about .750 inches. On one side of the gap, and preferably on an exterior surface of the PVC body 60, is a seal flap 51. Flap 51 preferably is formed a relatively soft material which may be fixed by a suitable means, such as glue, to the PVC body 60. A similar flap 53 may be provided on an exterior surface on the other side of the gap 57. If desired, a slit with no spacing or a small slot or gap 57 with a nominal spacing may be provided between the ends of the flaps 51, 53, which also may overlap. The sheath 50 may thus be used to contain hot rising gas circumferentially about the bottle 55 for efficient heating of the bottle. When installed on the bottle, a portion of the valve stem and the handle 54 for controlling the valve 52 extends radially outward from the sheath and between the soft seal flaps.

In certain circumstances, it may be desirable or mandatory to avoid venting the cold fluid and the hot fluid from the sampling system. In a typical application, only approximately 60 cubic feet of natural gas is necessary to desirably heat both the probe and the bottle 55 for a bottle filling operation. If cold gas from the line 32 is not vented to the atmosphere, it may be passed along line 164 to a treatment unit 166, where possibly harmful or noxious components of the gas may be effectively treated or filtered such that the discharge from the treatment unit 166 may now be released to the atmosphere. In other applications, a flare unit 168 may be used for flaring the hydrocarbon containing gas, which may be treated or untreated by the treatment unit 166. In still other applications, the cold fluid may or may not pass through a treatment unit 166 before being stored in a storage vessel 176. In still another application, the cold fluid from line 32 could pass along line 160 and be pumped back into the pipeline by the pump 162. In most applications, however, electric power for a pump will not be readily available since, as previously explained, many of these sampling probes are located in remote areas. It may be possible, however, to provide a battery powered pump 162. In other applications, a small pump driven by the natural gas passing through the pipeline 50 may use the energy of this pipeline moving gas to power a pump so that the discharge from the pump 162 is slightly above line pressure in the pipeline P. Although not shown, those skilled in the art will understand that a similar treatment unit, filtering unit, vessel, and pump could be provided for containing or otherwise treating the hot gas that exits from the top of the sample bottle 55.

In a typical application, pipeline P may be transporting natural gas at a pressure of from 100 psig to 1000 psig, and the regulator 24 may be set at a preselected (or adjustable, if desired) pressure level of 90 psi for supplying regulated pressurized fluid to the vortex heater 34.

In some applications, it may be cost effective for the sampling technician to bring a portable pressurized gas container to the test site for heating the probe and sample bottle when conducting the test. For example, there may be a sufficiently high hydrogen sulfide content in the gas that it may not be cost effective or permissible to either treat or allow the release of the gas to the environment. In those applications, the bottle 55 may thus be brought to the test site by the technician with a vacuum in the bottle.

A pressurized bottle 172 containing a suitable pressurized gas, such as air, may thus be brought to the test site by the sampling technician. Line 174 from the bottle 172 may optionally be connected to a 3-way valve 178. When in one position, the valve 178 is open to provide communication along line 30 to the heater body 34. In yet another position, the valve 178 may transmit fluid from the line 174 to the heater body 34, and while in a third position the valve 178 may close off the ends of both the line 174 and the line 30. When properly positioned to receive pressurized fluid from the line 174, the valve 176 may thus be opened by the sampling technician and a quantity of pressurized air provided to the vortex heater 34. Since the warming fluid is air, fluid from the cold fluid line 32 may be vented to atmosphere, and hot fluid passed through the probe to warm the probe and, in a preferred application, also the bottle 55, before the air is vented through the top end of the sheath 50.

One potential problem with the embodiment described above is that when the pipeline pressure is high, the pressure drop in the regulator cools the low pressure outlet air. The vortex heater may only shift the supply gas temperature by a set amount. As the supply air cools the regulator, the vortex heater output temperature is also cooler. Conceptionally, however, there are various ways of warming the supply air using the waste heat. The vortex supply line 30 may be coiled about hot gas outlet tube 36 to pre-warm the supply to vortex heater 34. Alternately, a finned heat exchanger could be attached to line 30 to transfer ambient air heat to the cold supply line 30.

The present invention is primarily directed to providing an improved system and method for spot sampling, as described above. Equipment and methods as describe herein may also be used for performing improved composite sampling. The vortex heater may thus heat the composite sampling probe and preferably the bottle which contains the composite sample. Venting of the gas may not be acceptable, and accordingly techniques for returning of all or most of the cold gas and/or the hot gas to the pipeline may be used to overcome these concerns. Alternatively, all or part of the hot or cold fluid may be treated or captured in a receiving vessel, as disclosed herein.

Although the invention has thus been described in detail for these embodiments, it should be understood that this explanation is for illustration, and that the invention is not limited to these embodiments. Alternate sampling equipment and operating techniques will be apparent to those skilled in the art in view of this disclosure. Additional modifications are thus contemplated and may be made without departing from the spirit of the invention, which is defined by the claims.

What is claimed is:

1. A system for sampling gas flowing in a pipeline by collecting a fluid sample in a sampler bottle, the system comprising:
   a sample probe secured to and extending outward from the pipeline, the sample probe having a probe inlet for positioning within the gas flowing in the pipeline;
   a heater body removably securable to the probe for transmitting gas from the sample probe to the sampler bottle;
   a vortex heater for receiving gas from the pipeline and separately outputting a cold fluid and a hot fluid; and
   the heater body having a flow path therein for directing the hot fluid to heat the sample probe.

2. A system as defined in claim 1, wherein the sample probe is mounted directly to the heater body.

3. A system as defined in claim 2, further comprising:
   a pressure regulator for regulating gas pressure from the pipeline and outputting gas at a selected pressure lower than pipeline pressure to the vortex heater.

4. A system as defined in claim 1, wherein the cold fluid is vented to the atmosphere.

5. A system as defined in claim 1, wherein the sample probe includes an elongate incoming hot fluid flow passageway, an elongate outgoing hot fluid flow passageway and a connecting passageway fluidly connecting the incoming hot fluid flow passageway and the outgoing hot fluid flow passageway.

6. The system as defined in claim 5, wherein hot fluid discharged from the hot fluid flow passageway warms the sampler bottle.

7. A system as defined in claim 6, further comprising:
a bottle warming sheath substantially enclosing the bottle, the bottle sheath having elongate slit formed from a pliable material to provide a warming sheath while allowing the sheath to be placed on or removed from the sampler bottle while the sampler bottle is fluidly connected to the heater body.

8. The system as defined in claim 7, wherein the warming sheath is supported on the heater body and hot fluid is discharged from within the warming sheath to the environment through an upper end of the warming sheath.

9. The system as defined in claim 1, wherein the probe includes a probe valve for sealing gas in the pipeline; and
the probe includes an upper threaded end; and
a cover for threaded engagement with the upper threaded end of the probe to protect the probe when the heater body is not connected to the probe.

10. The system as defined in claim 1, wherein the sample probe includes a lower inlet valve and upper exhaust valve each for controlling gas flow into and from the bottle, respectively.

11. The system as defined in claim 1, wherein the probe includes a gas passageway for transmitting gas from the pipeline to the heater body; and
at least a lower portion of the gas passageway positioned withing the pipeline includes an irregular sidewall to aid in retention of condensation.

12. The system as defined in claim 1, further comprising:
a locating pin for rotationally aligning the probe and the heater body for interconnection.

13. A system for sampling a hydrocarbon containing gas flowing in pipeline by collecting a gas sample in a sampler bottle, a system comprising;
a sample probe secured to and extending outward from the pipeline, the sample probe having a probe inlet for positioning within the hydrocarbon containing gas flowing in the pipeline;
a heater body for transmitting the hydrocarbon containing gas from the sample probe to the sampler bottle;
a vortex heater for receiving a pressurized gas and outputting a cold fluid and a hot fluid; and
the heater body having a flow path therein for directing the hot fluid to heat the sample probe.

14. The system as defined in claim 13, further comprising:
a portable pressurized vessel for supplying pressurized gas to the vortex heater.

15. The system as defined in claim 13, further comprising:
a flare device for flaring the cold fluid.

16. The system as defined in claim 13, further comprising:
a vessel for containing the cold fluid from the vortex heater.

17. A method of sampling gas in a pipeline utilizing a sample probe secured to the pipeline and a sampler bottle, the sample probe having an inlet for positioning within the gas flowing in the pipeline, the method comprising:
(1) securing a heater body to the probe for transmitting sample gas from a sample probe to the sampler bottle;
(2) transmitting pressurized gas to a vortex heater and separately outputting from the vortex heater a cold fluid and a hot fluid;
(3) transmitting the hot fluid from the vortex heater through the heater body and then into the probe, thereby heating the probe;
(4) filling at least a portion of the sampler bottle with gas from the pipeline; and
(5) thereafter disconnecting the heater body, the vortex heater, and the sampler bottle from the probe.

18. The method as defined in claim 17, further comprising:
moving the vortex heater and the heater body from a first probe secured to the pipeline at a first location to a second probe secured to the pipeline at a second location.

19. The method as defined in claim 18, further comprising:
cleaning a gas sample path in the heater body to reduce contamination before connecting the heater body to the second probe at the second location.

20. The method as defined in claim 17, wherein pressurized gas is transmitted from the pipeline through the heater body and then to the vortex heater.

21. The method as defined in claim 17, wherein the pressurized gas is transmitted from a portable pressure gas vessel to the vortex heater.

22. The method as defined in claim 17, further comprising:
providing a warming sheath to retain the hot fluid about the bottle;
transmitting the hot fluid from the heater body into the warming sheath and exterior of the bottle.

23. The method as defined in claim 17, further comprising:
regulating the pressure of gas to the vortex heater.

24. The method as defined in claim 17, further comprising:
forming the heater body from aluminum.

25. The method as defined in claim 17, further comprising:
venting the cold fluid to the atmosphere.

26. The method as defined in claim 17, further comprising:
providing a gas shut-off on the probe, such that the probe gas shut-off may be normally closed and opened only when the heater body is connected to the probe.

27. The method as defined in claim 17, further comprising:
protecting a connection on the probe for engagement with the heater body with a cap.

* * * * *